(12) United States Patent
Deno et al.

(10) Patent No.: US 12,708,308 B2
(45) **Date of Patent: *Aug. 18, 2026**

(54) SYSTEM AND METHOD FOR MAPPING ARRHYTHMIC DRIVER SITES

(71) Applicant: St. Jude Medical, Cardiology Division, Inc., St. Paul, MN (US)

(72) Inventors: Don Curtis Deno, Andover, MN (US); Steve Kim, New York, NY (US); Fikri Goksu, Arden Hills, MN (US); Thomas Hartley, Menomonie, WI (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 338 days.

This patent is subject to a terminal disclaimer.

(21) Appl. No.: 18/469,968

(22) Filed: Sep. 19, 2023

(65) Prior Publication Data

US 2024/0050015 A1 Feb. 15, 2024

Related U.S. Application Data

(60) Continuation of application No. 17/469,572, filed on Sep. 8, 2021, now Pat. No. 11,793,442, which is a (Continued)

(51) Int. Cl.
*A61B 5/287* (2021.01)
*A61B 5/00* (2006.01)

(52) U.S. Cl.
CPC ............ *A61B 5/287* (2021.01); *A61B 5/6858* (2013.01); *A61B 2562/0209* (2013.01); *A61B 2562/043* (2013.01)

(58) Field of Classification Search
CPC ............ A61B 5/349; A61B 2562/0209; A61B 2562/043; A61B 5/361; A61B 5/367
See application file for complete search history.

(56) References Cited

U.S. PATENT DOCUMENTS 5,697,377 A 12/1997 Wittkampf
5,983,126 A 11/1999 Wittkampf
(Continued)

FOREIGN PATENT DOCUMENTS

CN 102362808 A 2/2012

OTHER PUBLICATIONS

"S-PO06-001 to S-PO06-120 ED-Fogel Richard", Heart Rhythm, vol. 16, No. 5, May 2019, pp. S522-S572.
(Continued)

*Primary Examiner* — Paula J Stice
(74) *Attorney, Agent, or Firm* — Wiley Rein LLP

(57) ABSTRACT

Arrhythmic foci and other driver sites can be mapped using a multi-dimensional catheter. For instance, using a clique of three or more electrodes on the multi-dimensional catheter, an electroanatomical mapping system can identify a maximum bipolar voltage and an average unipolar voltage. The ratio of the average unipolar voltage to the maximum bipolar voltage can be interpreted as an indication of whether a cardiac location is an arrhythmic focus. Alternatively, an evaluation region can be defined about location in the patient's heart. The evaluation includes a plurality of rods, each associated with a respective E-field loop having a respective maximum and minimum amplitude bipole axes, with the rods being defined by the maximum amplitude bipole axes. For a sufficient number of rods within the evaluation region, a focus score for the evaluation region can be computed to reflect rod orientation consistency within the evaluation region.

19 Claims, 12 Drawing Sheets

Related U.S. Application Data division of application No. 16/388,593, filed on Apr. 18, 2019, now Pat. No. 11,134,879.

(60) Provisional application No. 62/663,193, filed on Apr. 26, 2018.

(56) References Cited

U.S. PATENT DOCUMENTS

| | | | |
|---|---|---|---|
| 6,360,121 | B1 | 3/2002 | Shoda et al. |
| 6,466,811 | B1 | 10/2002 | Hassett |
| 6,640,119 | B1 | 10/2003 | Budd et al. |
| 6,728,562 | B1 | 4/2004 | Budd et al. |
| 6,939,309 | B1 | 9/2005 | Beatty et al. |
| 6,947,785 | B1 | 9/2005 | Beatty et al. |
| 6,978,168 | B2 | 12/2005 | Beatty et al. |
| 6,990,370 | B1 | 1/2006 | Beatty et al. |
| 7,263,397 | B2 | 8/2007 | Hauck et al. |
| 7,885,707 | B2 | 2/2011 | Hauck |
| 9,474,491 | B2 | 10/2016 | Li et al. |
| 9,833,157 | B2 | 12/2017 | El Haddad et al. |
| 10,076,260 | B2 | 9/2018 | Bokan et al. |
| 10,136,829 | B2 | 11/2018 | Deno et al. |
| 10,194,494 | B2 | 1/2019 | Joo |
| 10,456,057 | B2 | 10/2019 | Drakulic et al. |
| 10,555,680 | B2 | 2/2020 | Thakur et al. |
| 10,631,749 | B2 | 4/2020 | Rubenstein |
| 10,758,137 | B2 | 9/2020 | Deno et al. |
| 11,058,342 | B2 | 7/2021 | Botzer et al. |
| 11,134,879 | B2 * | 10/2021 | Deno ...................... A61B 5/72 |
| 11,793,442 | B2 * | 10/2023 | Deno .................. A61B 5/6858 |
| 2008/0188765 | A1 | 8/2008 | Stolarski et al. |
| 2016/0324485 | A1 | 11/2016 | Erdemir et al. |
| 2016/0331471 | A1 | 11/2016 | Deno et al. |
| 2017/0049348 | A1 | 2/2017 | Deno et al. |
| 2017/0079539 | A1 | 3/2017 | Chauhan et al. |
| 2018/0042504 | A1 | 2/2018 | Botzer et al. |

OTHER PUBLICATIONS

International Search Report & Written Opinion received for PCT Application No. PCT/US2019/028175 dated Jul. 22, 2019, 15 pages.

* cited by examiner 13
200
204
206
216
208
17a
17b
17c
17d
17
214
210
212
218
202

700
706
702
704
13

SYSTEM AND METHOD FOR MAPPING ARRHYTHMIC DRIVER SITES

CROSS-REFERENCE TO RELATED APPLICATIONS

This application is a continuation of U.S. application Ser. No. 17/469,572, filed 8 Sep. 2021 ("the '572 application"), now U.S. Pat. No. 11,793,442, which is a divisional of U.S. application Ser. No. 16/388,593, filed 18 Apr. 2019 ("the '593 application"), now U.S. Pat. No. 11,134,879, which claims the benefit of U.S. provisional application No. 62/663,193, filed 26 Apr. 2018 ("the '193 provisional"). The '572 application, the '593 application, and the '193 provisional are hereby incorporated by reference as though fully set forth herein.

BACKGROUND

The present disclosure relates generally to electrophysiological mapping, such as may be performed in cardiac diagnostic and therapeutic procedures. In particular, the present disclosure relates to systems, apparatuses, and methods for mapping arrhythmic driver sites, such as arrhythmic foci.

Among the mechanisms believed to initiate and maintain atrial fibrillation ("AF") is the existence of localized drivers from which activation waves spread out, collide with one another, and produce the chaotic electrograms that can accompany AF (referred to herein as "arrhythmic foci"). It is believed that targeted ablation of these foci, while avoiding collateral damage to nearby structures such as the phrenic nerve, will terminate and prevent AF from recurring and minimize the likelihood of tamponade that can result from multiple ablation procedures.

Accurately locating arrhythmic foci, however, can be complicated. For instance, when using local activation timing ("LAT") maps, locating a focus to within a few millimeters requires timing to be determined accurately to within a few milliseconds. Timing measurements, however, can be impacted by changes in electrogram shape. Catheter design can also impact location accuracy.

BRIEF SUMMARY

Disclosed herein is a method of mapping arrhythmic foci using electrophysiological measurements made by a multi-dimensional catheter. The method includes, for a location in a patient's heart at which an electrophysiology data point is collected using the multi-dimensional catheter, the following steps: identifying a clique of three or more electrodes carried by the multi-dimensional catheter; identifying a maximum bipolar voltage for the clique of three or more electrodes; computing an average unipolar voltage for the clique of three or more electrodes; and computing a focus score using a ratio of the computed average unipolar voltage for the clique of three electrodes to the identified maximum bipolar voltage for the clique of three or more electrodes. The average unipolar voltage can be computed as an average peak-to-peak voltage or as an average peak-negative voltage.

The location in the patient's heart at which the electrophysiology data point is collected can be identified as a focal source when the focus score exceeds a preset threshold.

The steps of identifying a clique of three or more electrodes carried by the multi-dimensional catheter; identifying a maximum bipolar voltage for the clique of three or more electrodes; computing an average unipolar voltage for the clique of three or more electrodes; and computing a focus score using a ratio of the computed average unipolar voltage for the clique of three electrodes to the identified maximum bipolar voltage for the clique of three or more electrodes can be repeated for a plurality of locations in the patient's heart, thereby generating a focus score map. In aspects of the disclosure, the method includes outputting a graphical representation of the focus score map on a three-dimensional anatomical model.

In embodiments of the disclosure, the clique of three or more electrodes carried by the multi-dimensional catheter is a clique of four electrodes carried by the multi-dimensional catheter.

Also disclosed herein is a method of mapping arrhythmic foci using electrophysiological measurements made by a multi-dimensional catheter. The method includes, for a location in a patient's heart at which an electrophysiology data point is collected using the multi-dimensional catheter, the following steps: defining an evaluation region about the location in the patient's heart, the evaluation region encompassing a plurality of rods, wherein each rod of the plurality of rods is associated with a respective E-field loop having a respective maximum amplitude bipole axis and a respective minimum amplitude bipole axis, and wherein the rod is defined using the respective maximum amplitude bipole axis of the E-field loop; computing a rod orientation confidence score for the evaluation region; and when the rod orientation confidence score exceeds a preset rod orientation confidence threshold, computing a focus score for the evaluation region, wherein the focus score is indicative of rod orientation consistency within the evaluation region.

In aspects of the disclosure, the step of defining an evaluation region about the location in the patient's heart includes defining a spherical region about the location in the patient's heart. Alternatively, the step of defining an evaluation region about the location in the patient's heart can include defining the evaluation region to encompass a plurality of electrodes carried by the multi-dimensional catheter.

According to aspects of the disclosure, the step of computing a rod orientation confidence score for the evaluation region can include identifying a subset of the plurality of rods having associated respective maximum amplitude bipole axes that exceed a preset threshold magnitude. The preset threshold magnitude can be defined with reference to an electrogram noise floor, such as about twice the electrogram noise floor.

In other aspects of the disclosure, the step of computing a rod orientation confidence score for the evaluation region can include identifying a subset of the plurality of rods having associated respective E-field loop eccentricities in excess of a preset eccentricity threshold.

It is contemplated that the step of computing a focus score for the evaluation region can include conducting a principal component analysis of antipodal points of the plurality of rods. Alternatively, the step of computing a focus score for the evaluation region can include computing a mean pairwise dot product for the plurality of rods.

In still other embodiments, the step of computing a focus score for the evaluation region can include: defining a plurality of directions; for each direction, computing a mean dot product of a plurality of dot products computed between (1) each rod of the plurality of rods and (2) a unit vector in the respective direction; and identifying a direction of the plurality of directions having a greatest computed mean dot product.

In further embodiments, the step of computing a focus score for the evaluation region can include, for each rod of the plurality of rods: defining a unit vector extending from a center of the evaluation region to a midpoint of the rod; and computing a dot product between the rod and the unit vector, thereby computing a plurality of dot products; and computing a mean of the plurality of dot products.

The steps of defining an evaluation region about the location in the patient's heart, the evaluation region encompassing a plurality of rods, wherein each rod of the plurality of rods is associated with a respective E-field loop having a respective maximum amplitude bipole axis and a respective minimum amplitude bipole axis, and wherein the rod is defined using the respective maximum amplitude bipole axis of the E-field loop; computing a rod orientation confidence score for the evaluation region; and when the rod orientation confidence score exceeds a preset rod orientation confidence threshold, computing a focus score for the evaluation region, wherein the focus score is indicative of rod orientation consistency within the evaluation region can be repeated for a plurality of locations in the patient's heart, thereby generating a focus score map. The method can optionally include outputting a graphical representation of the focus score map on a three-dimensional anatomical model.

Also disclosed herein is an electroanatomical mapping system for mapping arrhythmic foci, including a focus mapping module configured: to receive as input an electrophysiology data point collected via a multi-dimensional catheter; to identify a clique of three or more electrodes carried by the multi-dimensional catheter; to identify a maximum bipolar voltage for the clique of three or more electrodes; to compute an average unipolar voltage for the clique of three or more electrodes; and to compute a focus score using a ratio of the computed average unipolar voltage for the clique of three electrodes to the identified maximum bipolar voltage for the clique of three or more electrodes.

The instant disclosure also provides an electroanatomical mapping system for mapping arrhythmic foci, including a focus mapping module configured: to receive as input an electrophysiology data point collected via a multi-dimensional catheter at a location in a patient's heart; to define an evaluation region about the location in the patient's heart, the evaluation region encompassing a plurality of rods, wherein each rod of the plurality of rods is associated with a respective E-field loop having a respective maximum amplitude bipole axis and a respective minimum amplitude bipole axis, and wherein the rod is defined using the respective maximum amplitude bipole axis of the E-field loop; to compute a rod orientation confidence score for the evaluation region; and when the rod orientation confidence score exceeds a preset rod orientation confidence threshold, to compute a focus score for the evaluation region, wherein the focus score is indicative of rod orientation consistency within the evaluation region.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for the creation of electrophysiology maps (e.g., electrocardiographic maps) that provide information regarding cardiac activity. Certain embodiments of the disclosure will be explained with reference to the use of a high density grid ("HD") grid catheter, such as the Advisor™ HD grid mapping catheter from Abbott Laboratories, to create electrophysiology maps, and in particular to create maps of arrhythmic foci. Aspects of the disclosure will be described in detail herein in the context of a cardiac mapping procedure carried out using an electrophysiology mapping system (e.g., using an electroanatomical mapping system such as the EnSite Precision™ cardiac mapping system from Abbott Laboratories).

Figure 1:
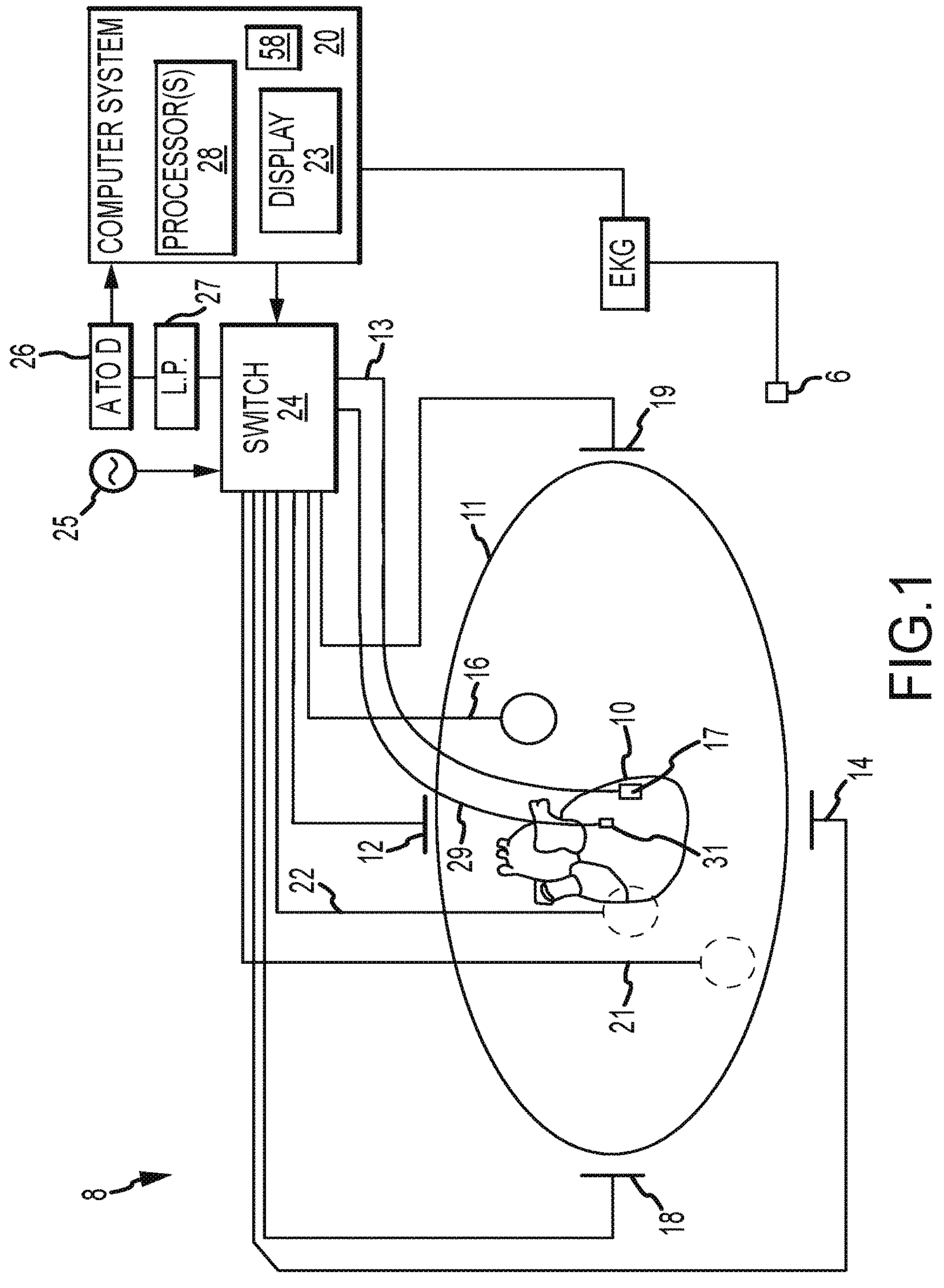
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes.

Figure 2:
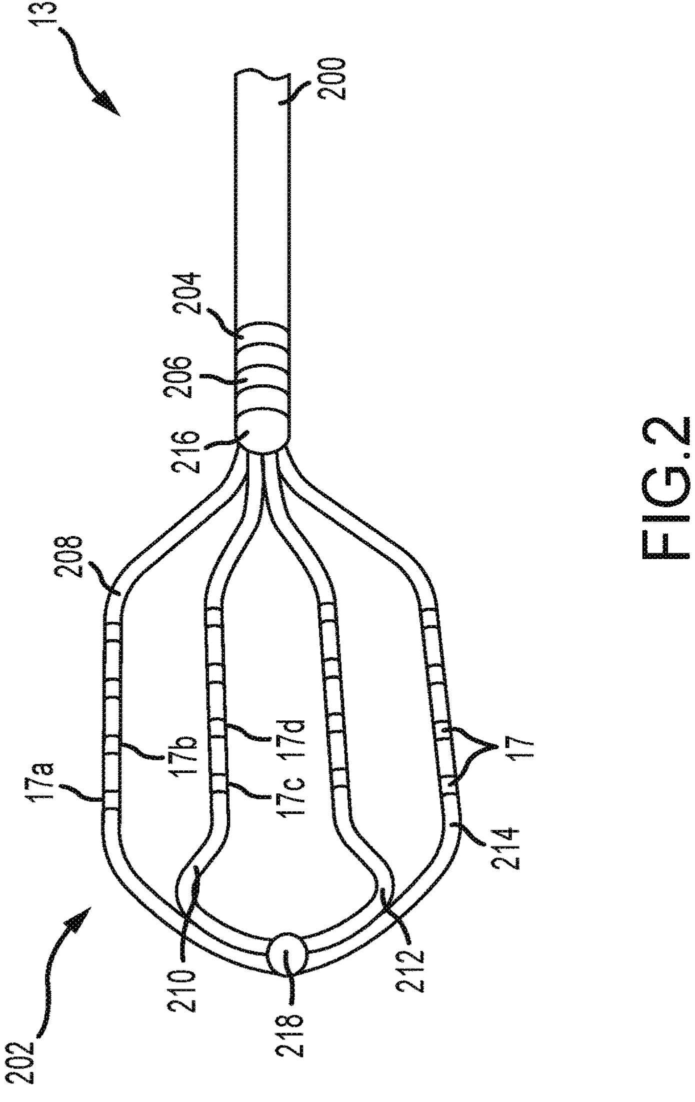
FIG. 2 depicts an exemplary catheter that can be used in connection with aspects of the instant disclosure.

The foregoing embodiments are merely exemplary, however, and any number of electrodes and/or catheters may be used. For example, for purposes of this disclosure, a segment of an exemplary multi-electrode catheter, and in particular an HD grid catheter, is shown in FIG. 2. HD grid catheter 13 includes a catheter body 200 coupled to a paddle 202. Catheter body 200 can further include first and second body electrodes 204, 206, respectively. Paddle 202 can include a first spline 208, a second spline 210, a third spline 212, and a fourth spline 214, which are coupled to catheter body 200 by a proximal coupler 216 and to each other by a distal coupler 218. In one embodiment, first spline 208 and fourth spline 214 can be one continuous segment and second spline 210 and third spline 212 can be another continuous segment. In other embodiments, the various splines 208, 210, 212, 214 can be separate segments coupled to each other (e.g., by proximal and distal couplers 216, 218, respectively). It should be understood that HD catheter 13 can include any number of splines and/or arrangements of electrodes on the splines; the four-spline arrangement shown in FIG. 2 is merely exemplary.

As described above, splines 208, 210, 212, 214 can include any number of electrodes 17; in FIG. 2, sixteen electrodes 17 are shown arranged in a four-by-four array. It should also be understood that electrodes 17 can be evenly and/or unevenly spaced, as measured both along and between splines 208, 210, 212, 214.

Catheter 13 (or multiple such catheters) are typically introduced into the heart and/or vasculature of the patient via one or more introducers and using familiar procedures. Indeed, various approaches to introduce catheter 13 into a patient's heart, such as transseptal approaches, will be familiar to those of ordinary skill in the art, and therefore need not be further described herein.

Since each electrode 17 lies within the patient, location data may be collected simultaneously for each electrode 17 by system 8. Similarly, each electrode 17 can be used to gather electrophysiological data from the cardiac surface (e.g., surface electrograms). The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation of a cardiac geometry and/or of cardiac electrical activity from the plurality of electrophysiology data points. Moreover, insofar as the ordinarily skilled artisan will appreciate how to create electrophysiology maps from electrophysiology data points, the aspects thereof will only be described herein to the extent necessary to understand the present disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation, the CARTO navigation and location system of Biosense Webster, Inc., the AURORA® system of Northern Digital Inc., Sterotaxis' NIOBE® Magnetic Navigation System, as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to mapping arrhythmic foci. Accordingly, system 8 can also include a focus mapping module 58. Focus mapping module 58 can be used, inter alia, to identify likely locations on the cardiac surface that are focal sources, as discussed in detail below.

Figure 3:
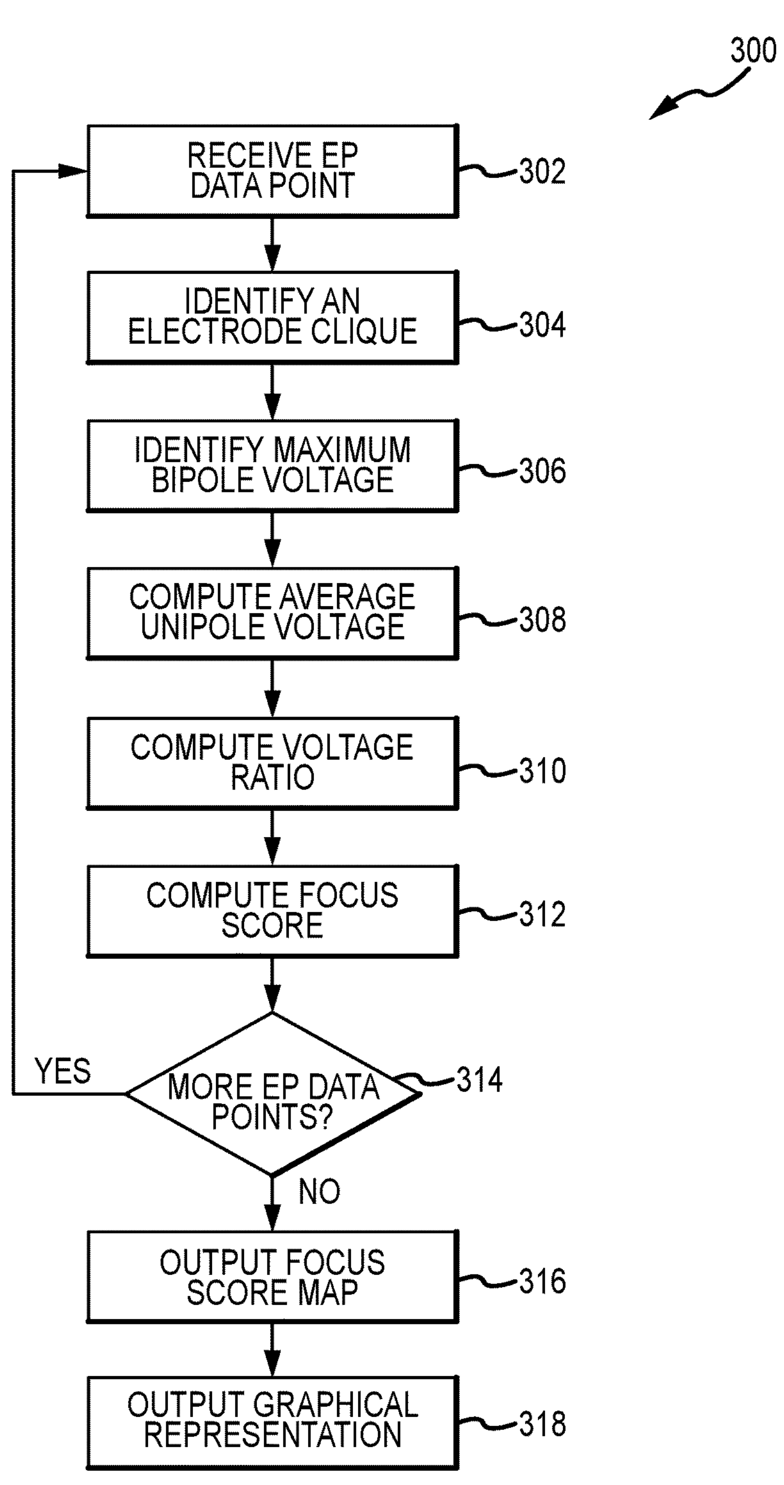
FIG. 3 is a flowchart of representative steps that can be carried out to identify arrhythmic drivers based on the magnitude of voltages measured by a multi-dimensional catheter according to a first embodiment disclosed herein.

One exemplary method of mapping arrhythmic foci according to the present teachings will be explained with reference to the flowchart 300 of representative steps presented as FIG. 3. In some embodiments, for example, flowchart 300 may represent several exemplary steps that can be carried out by electroanatomical mapping system 8 of FIG. 1 (e.g., by processor 28 and/or focus mapping module 58). It should be understood that the representative steps described below can be either hardware- or software-implemented. For the sake of explanation, the term "signal processor" is used herein to describe both hardware- and software-based implementations of the teachings herein.

In block 302, system 8 receives an electrophysiology data point, e.g., as collected by multi-dimensional catheter 13. As will be familiar to those of ordinary skill in the art, the electrophysiology data point received in block 302 will include both location data (e.g., a position of multi-dimensional catheter 13 within heart 10) and electrophysiological data (e.g., a series of electrograms measured by electrodes 17).

In block 304, system 8 identifies a clique of three or more electrodes 17 carried by multi-dimensional catheter 13. Consider, for example, a clique of four electrodes 17*a*, 17*b*, 17*c*, 17*d* as shown in FIG. 2. This clique includes a total of six possible bipoles: 17*a*-17*b* and 17*c*-17*d* along splines; 17*a*-17*c* and 17*b*-17*d* across splines; and 17*a*-17*d* and 17*b*-17*c* diagonally.

Similarly, consider a clique of three electrodes 17*a*, 17*b*, and 17*c* as shown in FIG. 2. This clique includes a total of three possible bipoles: 17*a*-17*b* along spline 208; 17*a*-17*c* across splines; and 17*b*-17*c* diagonally.

In block 306, system 8 identifies the maximum bipole voltage for the clique of electrodes 17. Typically, the maximum bipole voltage will be the maximum peak-to-peak voltage between bipoles of the clique (e.g., six bipoles in the case of a four-electrode clique; three bipoles in the case of a three-electrode clique).

In block 308, system 8 computes an average unipolar voltage for the clique of electrodes 17. Unipolar voltages for electrodes 17 can be computed as peak-to-peak voltages and/or as peak-negative voltages.

Near an arrhythmic focus, the bipolar voltage in any direction is close to zero, but unipolar voltage is relatively large. Thus, in block 310, system 8 computes a ratio of the average unipolar voltage for the clique of electrodes 17 to the maximum bipolar voltage for the clique of electrodes 17. The larger this ratio, the more likely the location is an arrhythmic focus.

The ratio of average unipolar voltage to maximum bipolar voltage can also be used in block 312 to compute a numerical indication of the likelihood that the location is an arrhythmic focus (a numerical indication of the likelihood that a location is an arrhythmic focus is referred to herein as a "focus score"). In some embodiments, the ratio itself can be defined as the focus score; in other embodiments of the disclosure, the ratio can be used to compute the focus score (e.g., by taking the reciprocal and/or the logarithm of the ratio).

More particularly, if the focus score exceeds a preset threshold, it indicates that the location may be an arrhythmic focus. The threshold can be user-defined. In embodiments of the disclosure, however, the threshold is a ratio of average unipolar voltage to maximum bipolar voltage between about 2 and about 4.

Decision block 314 initiates a loop to process any additional electrophysiology data points. Once all electrophysiology data points are processed, however, system 8 outputs a focus score map in block 316. In block 318, system 8 can output a graphical representation of the focus score map, for example on a three-dimensional cardiac model according to techniques that will be familiar to those of ordinary skill in the art.

Figure 4:
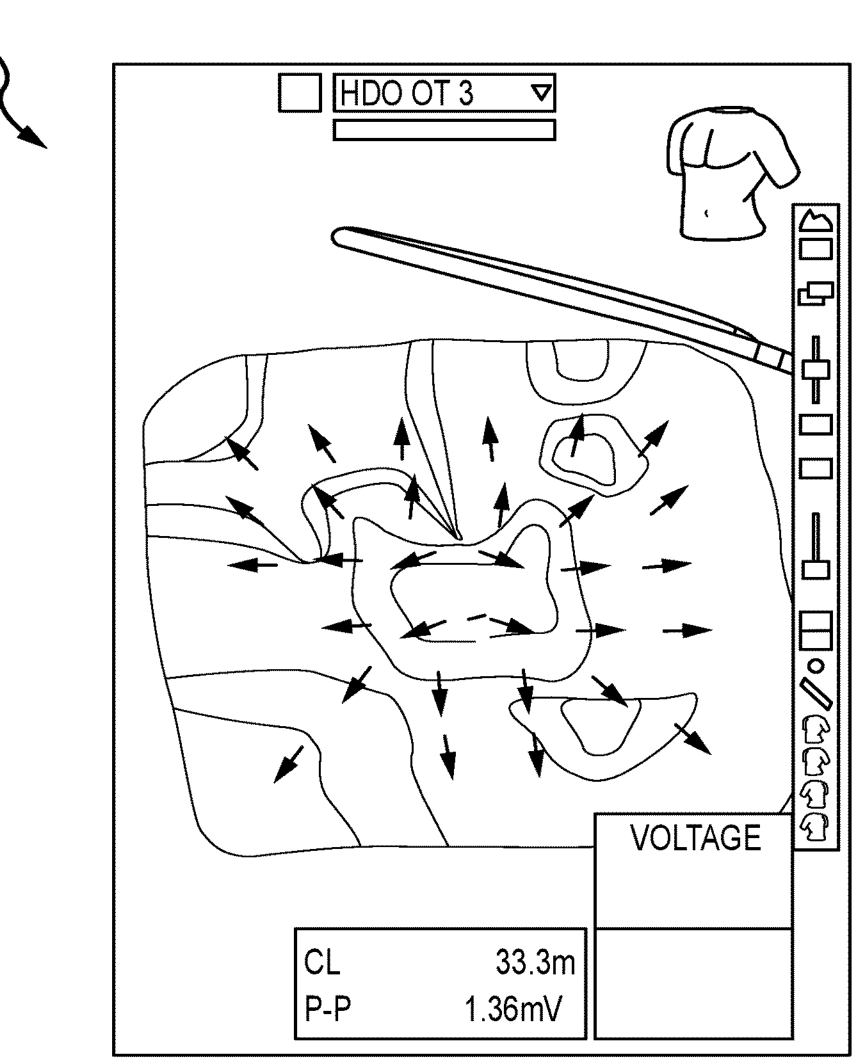
FIG. 4 graphically depicts an exemplary focus score map created according to the representative steps shown in FIG. 3.

FIG. 4 depicts a representative focus score map 400. As shown in FIG. 4, the dark region at the center has the highest ratio of average unipolar voltage to maximum bipolar voltage, and thus is the most likely location of an arrhythmic focus.

Figure 5:
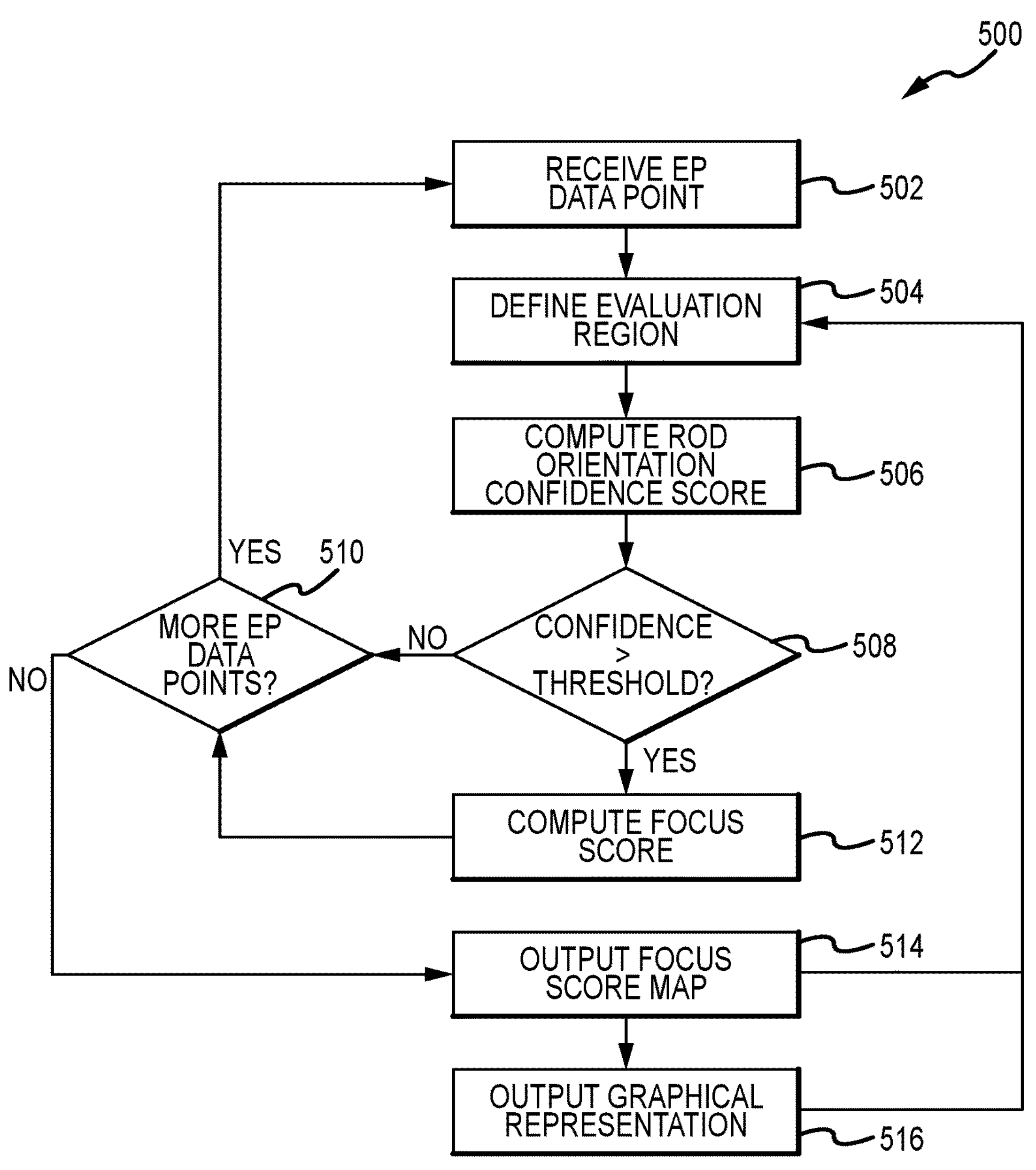
FIG. 5 is a flowchart of representative steps that can be carried out to identify arrhythmic drivers based on the relative direction of maximum bipole axes measured by a multi-dimensional catheter according to a second embodiment disclosed herein.

Another exemplary method of mapping arrhythmic foci according to the present teachings is shown in the flowchart 500 of representative steps presented as FIG. 5. In some embodiments of the disclosure, flowchart 500 may represent several exemplary steps that can be carried out by electroanatomical mapping system 8 of FIG. 1 (e.g., by processor 28 and/or focus mapping module 58). It should be understood that the representative steps of FIG. 5 can be either hardware- or software-implemented.

In block 502, system 8 receives an electrophysiology data point, e.g., as collected by multi-dimensional catheter 13. As will be familiar to those of ordinary skill in the art, the electrophysiology data point received in block 502 will include both location data (e.g., a position of multi-dimensional catheter 13 within heart 10) and electrophysiological data (e.g., a series of electrograms measured by electrodes 17).

In block 504, system 8 defines an evaluation region about the location of the electrophysiology data point received in block 502. The size of the evaluation region can take into account map point density, desired resolution, interelectrode spacing, and the expected extent over which an arrhythmic focus will exhibit radial propagation. In embodiments of the disclosure, the size of the evaluation region can also take into account the focus score computed in block 512, as shown by the loop from block 514 to block 504. Similarly, it is contemplated that the practitioner may desire to adjust the size of the evaluation region based on a visual evaluation of the focus score map computed in block 514, as shown by the loop from block 516 to block 504.

Figure 6:
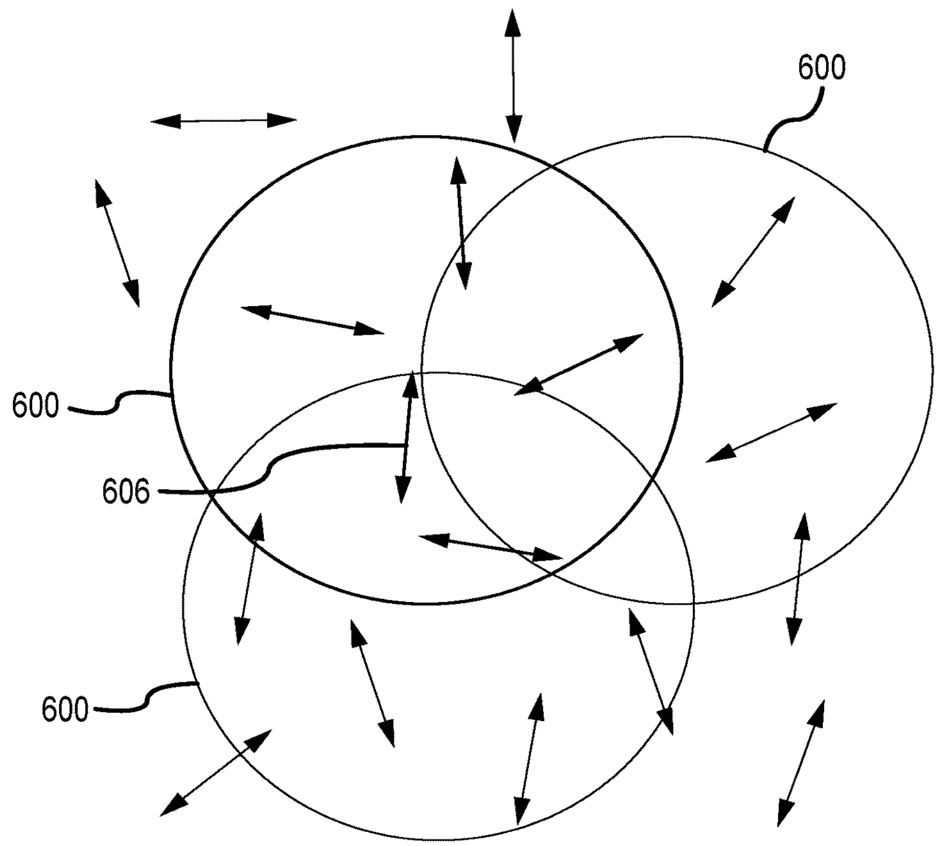
FIG. 6 depicts one approach to defining an evaluation region about an electrophysiology data point according to aspects of the instant disclosure.

As shown in FIG. 6, in some embodiments of the disclosure, the evaluation region is defined as a sphere 600 (e.g., a sphere having a radius of about 1 cm) centered at the location of the electrophysiology data point received in block 502. FIG. 6 also shows that it is desirable for adjacent spheres 600 to overlap.

Figure 7A:
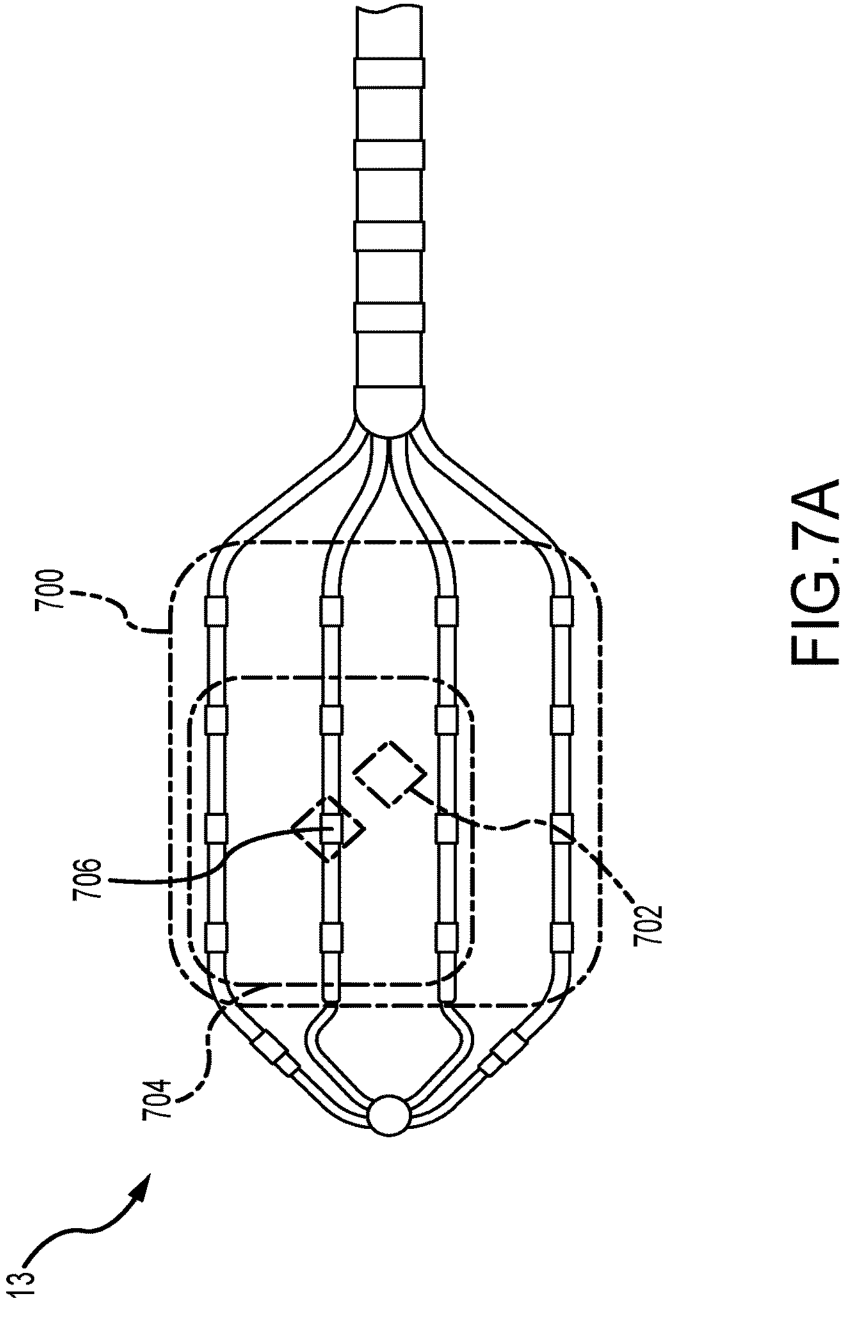
FIGS. 7A and 7B depict additional approaches to defining an evaluation region about an electrophysiology data point according to additional aspects of the instant disclosure.

In other embodiments of the disclosure, the evaluation region is defined with respect to electrodes 17 carried by multi-dimensional catheter 13. For instance, as shown in FIG. 7A, the evaluation region 700 can be defined to encompass all sixteen electrodes 17 on multi-dimensional catheter 13. Evaluation region 700 thus encompasses thirty-six three-electrode cliques, and thus a total of thirty-six bipoles. For purposes of analysis according to the teachings herein, these bipoles can be assigned to the center point 702 of evaluation region 700.

Figure 7B:
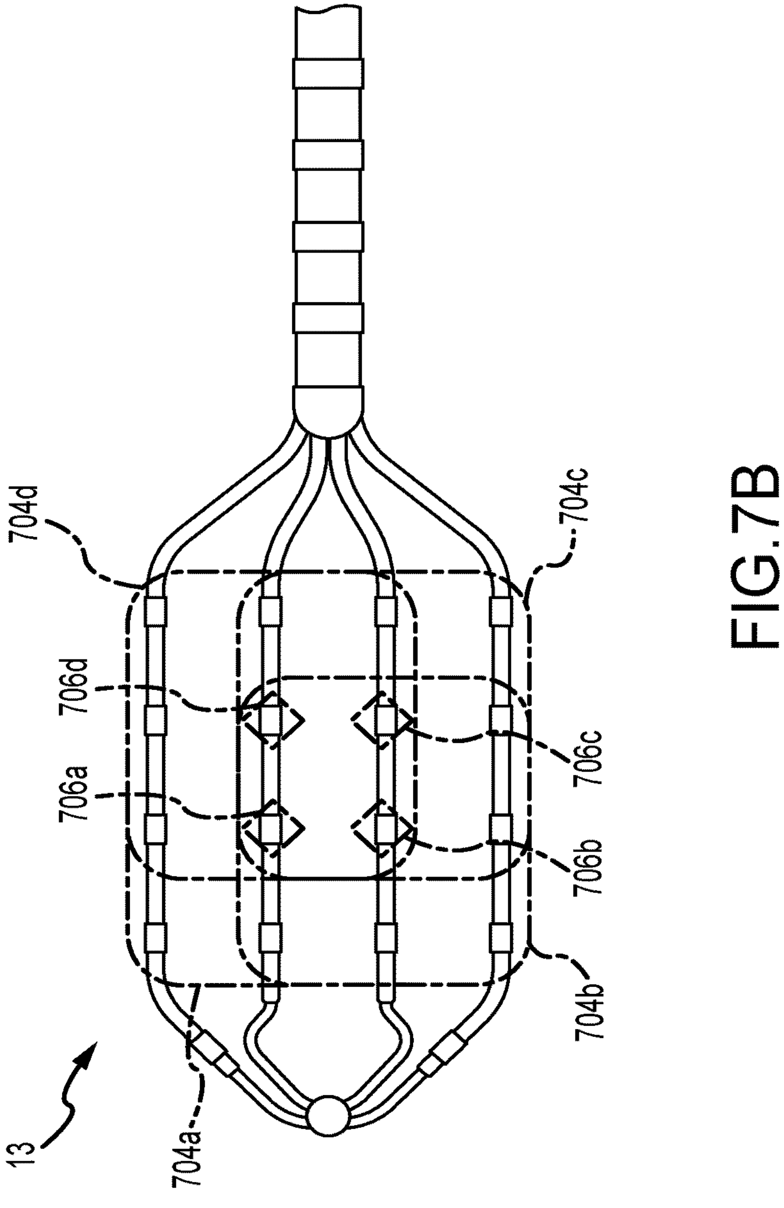

FIG. 7A also shows an evaluation region 704, having a center point 706, encompassing nine of the sixteen electrodes 17 on multi-dimensional catheter 13. As shown in FIG. 7B, there are four such regions 704*a*-704*d* that can be formed on multi-dimensional catheter 13, each having a corresponding center point 706*a*-706*d*. Each set of nine electrodes 17 encompasses sixteen three-electrode cliques, and thus a total of sixteen bipoles (which can be assigned to the respective center points 706*a*-706*d* for purposes of analysis as disclosed herein).

In any event, the evaluation region defined in block 504 includes a plurality of "rods" 602 (shown in FIG. 6 as dual-arrowed segments). As used herein, the term "rod" refers to the maximum amplitude bipole axis of a respective E-field loop for a clique of electrodes 17 on multi-dimensional catheter 13; the E-field loop will also have a minimum amplitude bipole axis. Details of computing an E-field loop for a clique of electrodes are described in U.S. application Ser. No. 15/953,155, which is hereby incorporated by reference as though fully set forth herein.

Near an arrhythmic focus, rods will be arranged radially about the focus rather than oriented uniformly (e.g., parallel) with respect to each other. Thus, in block 506, system 8 can compute a rod orientation confidence score for the evaluation region (e.g., 600, 700). The rod orientation confidence score is a measure of whether or not a given evaluation region (e.g., 600, 700) contains sufficient rods from which a valid inference about whether or not the evaluation region is an arrhythmic focus can be drawn.

In aspects of the disclosure, the rod orientation confidence score is computed by identifying a subset of the rods within the evaluation region that are defined by corresponding maximum amplitude bipole axes exceeding a preset threshold amount. In some embodiments, this preset threshold amount can be defined with respect to an electrogram noise floor (e.g., about 0.05 mV peak-to-peak), such as about twice the electrogram noise floor (e.g., about 0.1 mV peak-to-peak).

In other aspects of the disclosure, the rod orientation confidence score is computed by identifying a subset of the rods within the evaluation region that have corresponding E-field loop eccentricities in excess of a preset eccentricity threshold. Eccentricity of an E-field loop can be measured by a ratio of the maximum amplitude bipole axis to the minimum amplitude bipole axis. In embodiments, the eccentricity threshold is about 2 (e.g., the maximum amplitude bipole axis is at least twice the minimum amplitude bipole axis).

In decision block 508, system 8 determines whether the rod orientation confidence score exceeds a preset rod orientation confidence threshold. If not, decision block 510 initiates a loop to process any additional electrophysiology data points. If so, system 8 can compute a focus score in block 512 using the consistency of the orientation of the rods within the evaluation region. More particularly, because rod orientation is less consistent near an arrhythmic focus and more consistent further away from the arrhythmic focus, system 8 can interpret greater degrees of rod orientation consistency as lower likelihoods that the location is an arrhythmic focus. Various exemplary approaches to determining rod orientation consistency within the evaluation region will be discussed below.

Figure 8B:
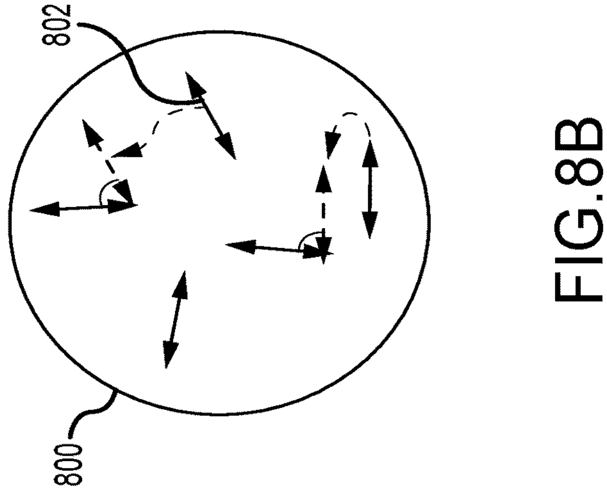
FIGS. 8A through 8D illustrate various approaches to determining rod orientation consistency.
Figure 8A:
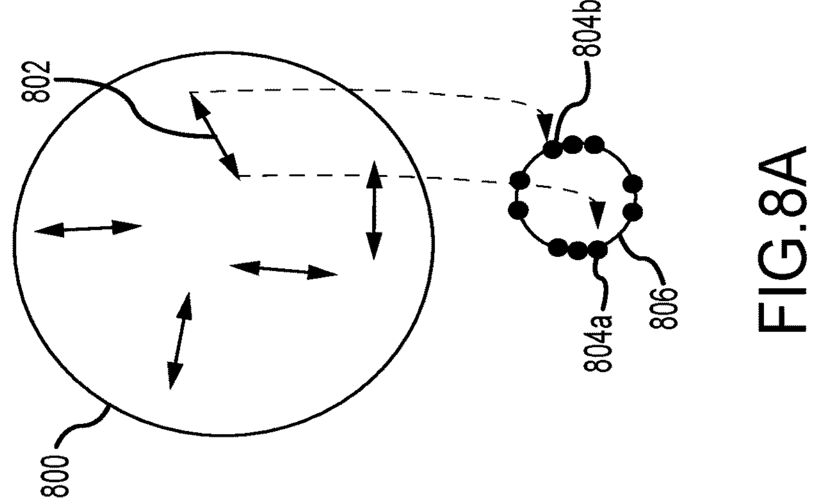

Principal component analysis of antipodal points. FIG. 8A illustrates a first approach to determining rod orientation consistency within an evaluation region 800 according to aspects of the instant disclosure. As shown in FIG. 8A, for each rod 802 within the orientation region, two antipodal points 804*a*, 804*b* are placed on a unit circle 806 (or, in three dimensions, a unit sphere) centered at the origin. System 8 then performs a principal component analysis on the antipodal points and computes a ratio of the greatest to the least (or next least) singular values. Larger ratios correspond to more consistently oriented rods 802. Thus, if the ratio is substantially greater than one (e.g., greater than about four), it indicates that rods 802 are nearly parallel, which in turn suggests that evaluation region 800 is not an arrhythmic focus. On the other hand, if the ratio is less than a critical value (e.g., about two), it suggests that evaluation region 800 likely contains an arrhythmic focus.

Mean of pairwise dot products between rods. FIG. 8B illustrates a second approach to determining rod orientation consistency within an evaluation region 800 according to aspects of the instant disclosure. System 8 computes the absolute value of the dot product of each pair of rods 802 within evaluation region 800. System 8 then computes the mean of these values. Larger means correspond to more consistently oriented rods 802. Thus, the larger the mean, the less likely evaluation region 800 contains an arrhythmic focus, and the smaller the mean, the more likely evaluation region 800 contains an arrhythmic focus.

Figure 8D:
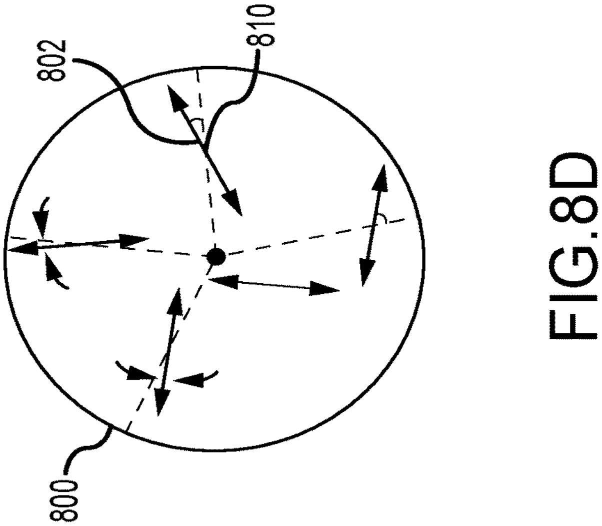
Figure 8C:
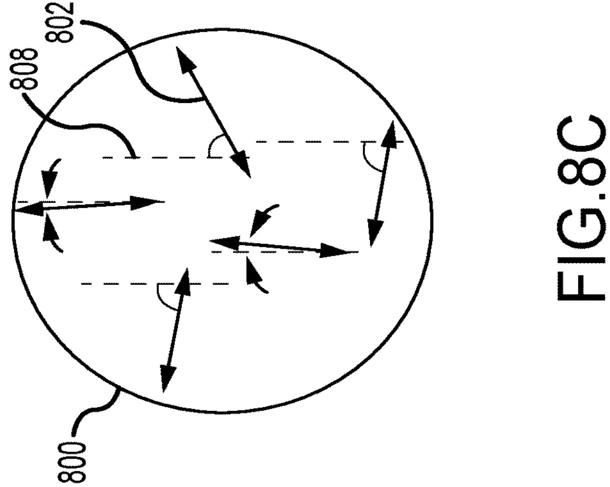

Maximum over possible angles of mean dot products between rods and possible angle unit vectors. FIG. 8C illustrates a third approach to determining rod orientation consistency within an evaluation region 800 according to aspects of the instant disclosure. System 8 defines a unit vector 808 in each of a plurality of directions. For the sake of clarity, FIG. 8C depicts only a single directional unit vector 808; it should be understood that this approach can use about 180 directional unit vectors 808 with a resolution of about 1 degree. For each direction, system 8 first computes the absolute value of the dot product between each rod 802 and the corresponding directional unit vector 808 and then computes the mean of these values. System 8 then identifies the direction having the greatest computed mean dot product. Larger means correspond to more consistently oriented rods 802. Thus, the larger the maximum mean dot product, the less likely evaluation region 800 contains an arrhythmic focus, and the smaller the maximum mean dot product, the more likely evaluation region 800 contains an arrhythmic focus.

Mean of dot products between rods and radially-oriented unit vectors. FIG. 8D illustrates a fourth approach to determining rod orientation consistency within an evaluation region 800 according to aspects of the instant disclosure. For each rod 802, system 8 defines a unit vector 810 extending from the center of evaluation region 800 to the midpoint of the rod 802. System 8 computes the absolute value of the dot product between unit vector 810 and rod 802, and then computes the mean of these values. In this approach, larger means correspond to less consistently oriented rods 802. Thus, the larger the maximum mean dot product, the more likely evaluation region 800 contains an arrhythmic focus, and the smaller the maximum mean dot product, the less likely evaluation region 800 contains an arrhythmic focus.

Decision block 510 initiates a loop to process any additional electrophysiology data points. Once all electrophysiology data points are processed, however, system 8 outputs a focus score map in block 514. In block 516, system 8 can output a graphical representation of the focus score map, for example on a three-dimensional cardiac model according to techniques that will be familiar to those of ordinary skill in the art.

Figure 9:
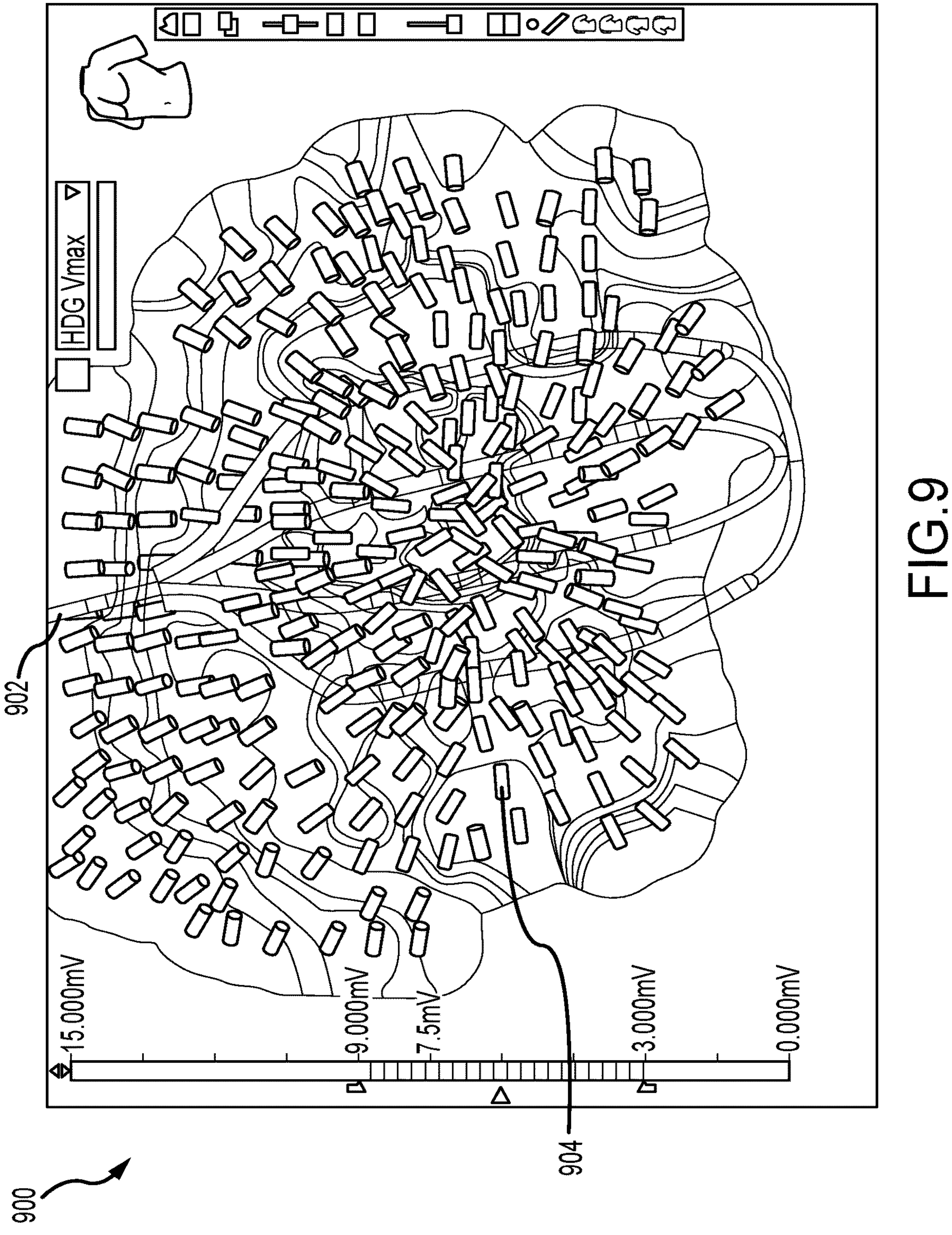
FIG. 9 graphically depicts an exemplary focus score map created according to the representative steps shown in FIG. 5.

FIG. 9 is a representative graphical representation 900 of a focus score map. Graphical representation 900 includes a representation 902 of multi-dimensional catheter 13 and graphical representations 904 of the plurality of rods described above. Near the center of FIG. 9, rods 904 are not consistently oriented, visually suggesting that they are proximate an arrhythmic focus. Further away from the center of FIG. 9, rods 904 are more consistently oriented, visually suggesting that they are not proximate (or, at least, less proximate) an arrhythmic focus.

Figure 10:
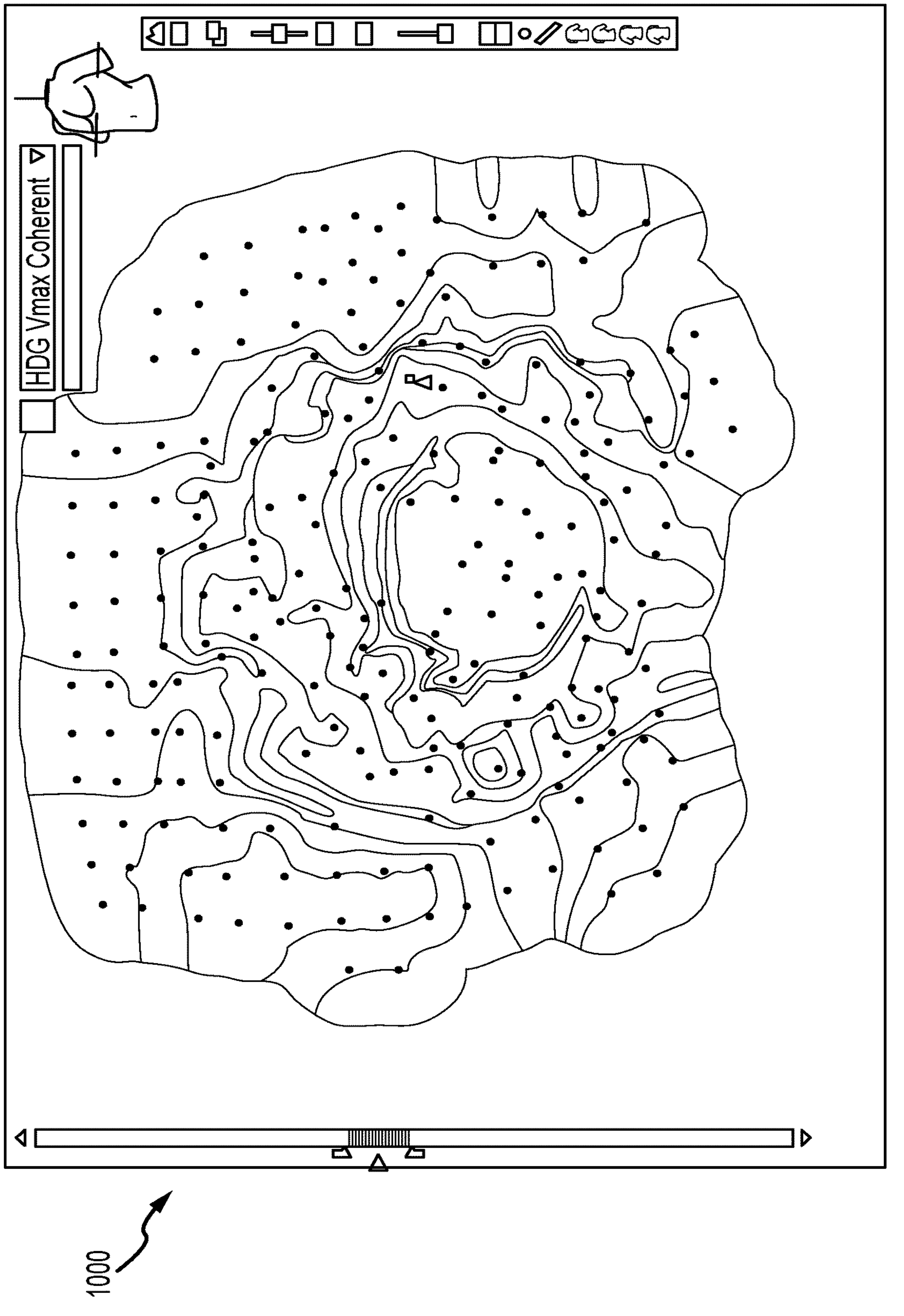
FIG. 10 graphically depicts an exemplary coherence map.

In aspects of the disclosure, system 8 can also output a coherency map; FIG. 10 is a graphical representation 1000 of such a map illustrating the degree to which the rods described above are parallel to each other. As shown in FIG. 10, areas of low coherency are shown in white or light grey, while areas of high coherency are shown in dark grey or black. Visually, areas of low coherency (e.g., white or light grey) are more likely to be arrhythmic foci than are areas of high coherency (e.g., dark grey or black).

Aspects of the disclosure also relate to distinguishing between other sites of interest during an electrophysiology study, such as breakout sites, source sites, collision sites, and sink sites. At sites where a focal source or region of breakout occurs, unipolar signals are predominantly negative-going (so-called "QS morphology"). Conversely, at sites where collisions or sinks occur, unipolar signals are almost entirely positive (so-called "R morphology").

Thus, embodiments disclosed herein can include assessing the unipolar deflection in order to identify the morphology and classify the region as, inter alia, a region of breakout or a region of collision. For instance, if the initial upward deflection is less than about 10% of the total peak-to-peak voltage, it can be interpreted as QS morphology, suggesting a region of breakout. Alternatively, if the downward deflection is less than about 10% of the total peak-to-peak voltage, it can be interpreted as R morphology, suggesting a region of collision or sink.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to electrophysiology data points collected during an electrophysiology study performed at an earlier time).

As another example, although aspects of the instant disclosure have been described in connection with identifying arrhythmic foci, the teachings herein can be applied to good advantage to identify other drivers (e.g., rotor sources).

As another example, rather than utilizing rods (e.g., maximum amplitude bipole axes), the teachings herein can be adapted to activation direction arrows. Similarly, rather than conducting a principal component analysis of antipodal points for a plurality of rods to determine a focus score for an evaluation region, the electroanatomical system described herein can determine a focus score for an evaluation region by computing an average of unit activation direction vector directions within the evaluation region. The computation of activation direction arrows (vectors) is described in U.S. Pat. No. 10,136,829, which is hereby incorporated by reference as though fully set forth herein. U.S. Pat. No. 9,474,491, which is also incorporated by reference as though fully set forth herein, teaches aspects of the computation of local conduction velocities, which teachings can also be applied when computing activation direction arrows (vectors).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electroanatomical mapping system for mapping arrhythmic foci, comprising:

a focus mapping module configured to:

receive, from each electrode of a clique of three or more electrodes carried by a multi-dimensional electrophysiology catheter, a respective unipolar electrogram signal;

compute, from the respective unipolar electrogram signals, an average unipolar voltage for the clique of three or more electrodes;

compute a maximum bipolar voltage for the clique of three or more electrodes; and compute a focus score for the clique of three or more electrodes using a ratio of the computed average unipolar voltage for the clique of three or more electrodes to the identified maximum bipolar voltage for the clique of three or more electrodes.

2. The electroanatomical mapping system according to claim 1, wherein the average unipolar voltage for the clique of three or more electrodes comprises an average peak-to-peak voltage for the clique of three or more electrodes.

3. The electroanatomical mapping system according to claim 1, wherein the average unipolar voltage for the clique of three or more electrodes comprises an average peak-negative voltage for the clique of three or more electrodes.

4. The electroanatomical mapping system according to claim 1, wherein the focus mapping module is further configured to:

identify a location in a patient's heart corresponding to a location of the clique of three or more electrodes; and define the location in the patient's heart as a focal source when the focus score exceeds a preset threshold.

5. The electroanatomical mapping system according to claim 1, wherein the focus mapping module is further configured to output a graphical representation of the focus score on a three-dimensional anatomical model of a patient's heart.

6. The electroanatomical mapping system according to claim 1, wherein the clique of three or more electrodes comprises a clique of four electrodes.

7. An electroanatomical mapping system for mapping arrhythmic foci, comprising:

a focus mapping module configured to:

receive as input a plurality of cardiac electrophysiology data points; and compute a focus score at a location in a patient's heart at which a selected cardiac electrophysiology data point of the plurality of cardiac electrophysiology data points was collected by:

defining an evaluation region about the location in the patient's heart, the evaluation region encompassing a plurality of rods, wherein each rod of the plurality of rods is defined by a maximum amplitude bipole axis of a respective E-field loop; and computing the focus score according to rod orientation consistency within the evaluation region.

8. The electroanatomical mapping system according to claim 7, wherein the focus mapping module is further configured to output a graphical representation of the focus score on a three-dimensional anatomical model of the patient's heart.

9. The electroanatomical mapping system according to claim 7, wherein the focus mapping module is further configured to compute a rod orientation confidence score for the evaluation region, and wherein the focus mapping module only computes the focus score at the location in the patient's heart when the rod orientation confidence score for the evaluation region exceeds a preset rod orientation confidence threshold.

10. The electroanatomical mapping system according to claim 9, wherein the rod orientation confidence score for the evaluation region is computed using a subset of the plurality of rods having respective maximum amplitude bipole axis that exceed a preset threshold magnitude.

11. The electroanatomical mapping system according to claim 10, wherein the preset threshold magnitude is defined with reference to an electrogram noise floor.

12. The electroanatomical mapping system according to claim 11, wherein the preset threshold magnitude comprises twice the electrogram noise floor.

13. The electroanatomical mapping system according to claim 9, wherein the rod orientation confidence score for the evaluation region is computed using a subset of the plurality of rods having respective E-field loop eccentricities that exceeds a preset eccentricity threshold.

14. The electroanatomical mapping system according to claim 7, wherein the evaluation region comprises a spherical region about the location in the patient's heart.

15. The electroanatomical mapping system according to claim 7, wherein the evaluation region encompasses a subset of the plurality of cardiac electrophysiology data points.

16. The electroanatomical mapping system according to claim 7, wherein the focus score is computed by conducting a principal component analysis of antipodal points of the plurality of rods.

17. The electroanatomical mapping system according to claim 7, wherein the focus score is computed by computing a mean pairwise dot product for the plurality of rods.

18. The electroanatomical mapping system according to claim 7, wherein the focus score is computed by the electroanatomical mapping system:

defining a plurality of directions;

for each direction of the plurality of directions, computing a mean dot product of a plurality of dot products computed between (1) each rod of the plurality of rods and (2) a unit vector in the respective direction; and identifying a direction of the plurality of directions having a greatest computed mean dot product.

19. The electroanatomical mapping system according to claim 7, wherein the focus score is computed by, for each rod of the plurality of rods, the electroanatomical mapping system:

defining a unit vector extending from a center of the evaluation region to a midpoint of the rod; and computing a dot product between the rod and the unit vector, thereby computing a plurality of dot products; and computing a mean of the plurality of dot products.

* * * * *